US008889082B2

(12) United States Patent
Muderlak et al.

(10) Patent No.: US 8,889,082 B2
(45) Date of Patent: Nov. 18, 2014

(54) APPARATUS FOR METERED DOSE OF ODOR CONTROL SUBSTANCE

(71) Applicant: Xela Innovations, LLC, Glendale, WI (US)

(72) Inventors: Todd J. Muderlak, Whitefish Bay, WI (US); Kenneth J. Muderlak, Milwaukee, WI (US)

(73) Assignee: San Jamar, Inc., Elkhorn, WI (US)

( * ) Notice: Subject to any disclaimer, the term of this patent is extended or adjusted under 35 U.S.C. 154(b) by 36 days.

(21) Appl. No.: 13/843,991

(22) Filed: Mar. 15, 2013

(65) Prior Publication Data

US 2014/0271376 A1    Sep. 18, 2014

(51) Int. Cl.
| | |
|---|---|
| *A61L 9/00* | (2006.01) |
| *A24F 25/00* | (2006.01) |
| *B01D 47/16* | (2006.01) |
| *A61L 9/12* | (2006.01) |

(52) U.S. Cl.
CPC ........ *A61L 9/127* (2013.01); *A61L 9/122* (2013.01)
USPC ............ 422/306; 239/34; 239/44; 261/94; 261/99; 261/100; 261/119.1; 222/1; 222/52; 222/63; 222/646

(58) Field of Classification Search
CPC ............... A61L 9/00; A61L 9/01; A61L 9/03; A61L 9/037; A61L 9/12; A61L 9/127
USPC ................. 422/5, 123, 306, 900; 239/34, 44; 261/94, 99–100, 119.1; 96/222; 222/1, 222/52, 63, 646
See application file for complete search history.

(56) References Cited

U.S. PATENT DOCUMENTS

| | | | |
|---|---|---|---|
| 5,114,625 | A | 5/1992 | Gibson |
| 5,249,718 | A | 10/1993 | Muderlak |
| 5,449,117 | A | 9/1995 | Muderlak et al. |
| 7,157,057 | B2 | 1/2007 | Gohil |
| 7,244,398 | B2 | 7/2007 | Kotary et al. |

(Continued)

FOREIGN PATENT DOCUMENTS

| | | |
|---|---|---|
| DE | 9402313 U1 | 3/1994 |
| EP | 0365770 A1 | 5/1990 |
| EP | 2564878 | 3/2013 |
| WO | 2012175972 | 12/2012 |

OTHER PUBLICATIONS

Communication Relating to the Results of the Partial International Search for PCT/US2013/067131, mailing date Feb. 25, 2014, 2 pages.

(Continued)

*Primary Examiner* — Monzer R Chorbaji
(74) *Attorney, Agent, or Firm* — Boyle Fredrickson, S.C.

(57) ABSTRACT

The present disclosure provides an apparatus for dispensing the fragrance of an odor control substance. The apparatus includes a housing defining a housing interior adapted to receive a refill component. The refill component includes a container with liquid odor control substance and a wick. The refill component is installed from the bottom into the housing for ease of servicing. A pump device in the housing dispenses a dose of the liquid odor control into a wicking area of the refill component. In another embodiment, the refill component includes the pump device. The pump device is installed into the housing when the refill component is replaced.

5 Claims, 8 Drawing Sheets

(56) References Cited

U.S. PATENT DOCUMENTS

| | | |
|---|---|---|
| 7,922,104 B2 | 4/2011 | Zlotnik et al. |
| 8,157,188 B2 | 4/2012 | Duston et al. |
| 2004/0265189 A1 | 12/2004 | Schwarz |
| 2006/0163376 A1 | 7/2006 | Lakatos et al. |
| 2006/0180143 A1 | 8/2006 | Lind et al. |
| 2007/0036673 A1* | 2/2007 | Selander .......................... 422/5 |
| 2009/0151061 A1 | 6/2009 | Chen |
| 2010/0147972 A1 | 6/2010 | Lakatos et al. |
| 2013/0032641 A1 | 2/2013 | Muderlak et al. |
| 2013/0034444 A1 | 2/2013 | Muderlak et al. |

OTHER PUBLICATIONS

PCT/US2014/030123, International Search Report and Written Opinion dated Jul. 7, 2014, 16 pages.

* cited by examiner

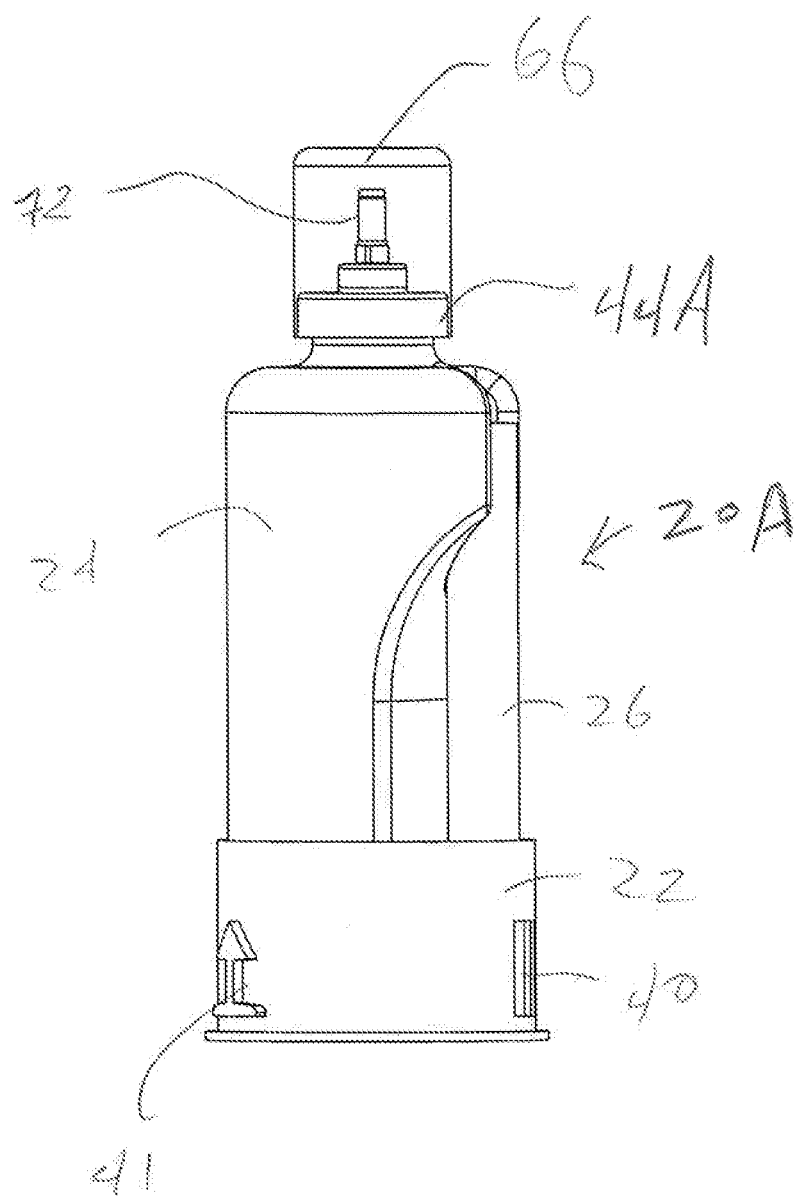

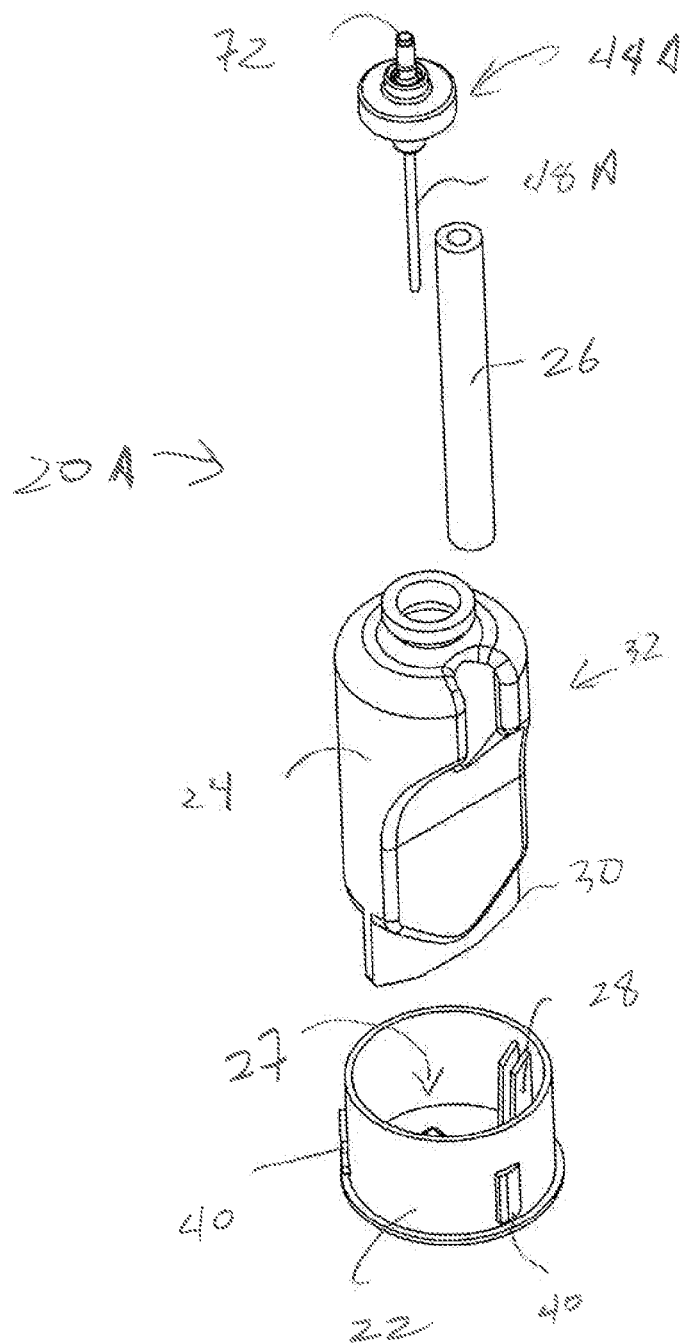

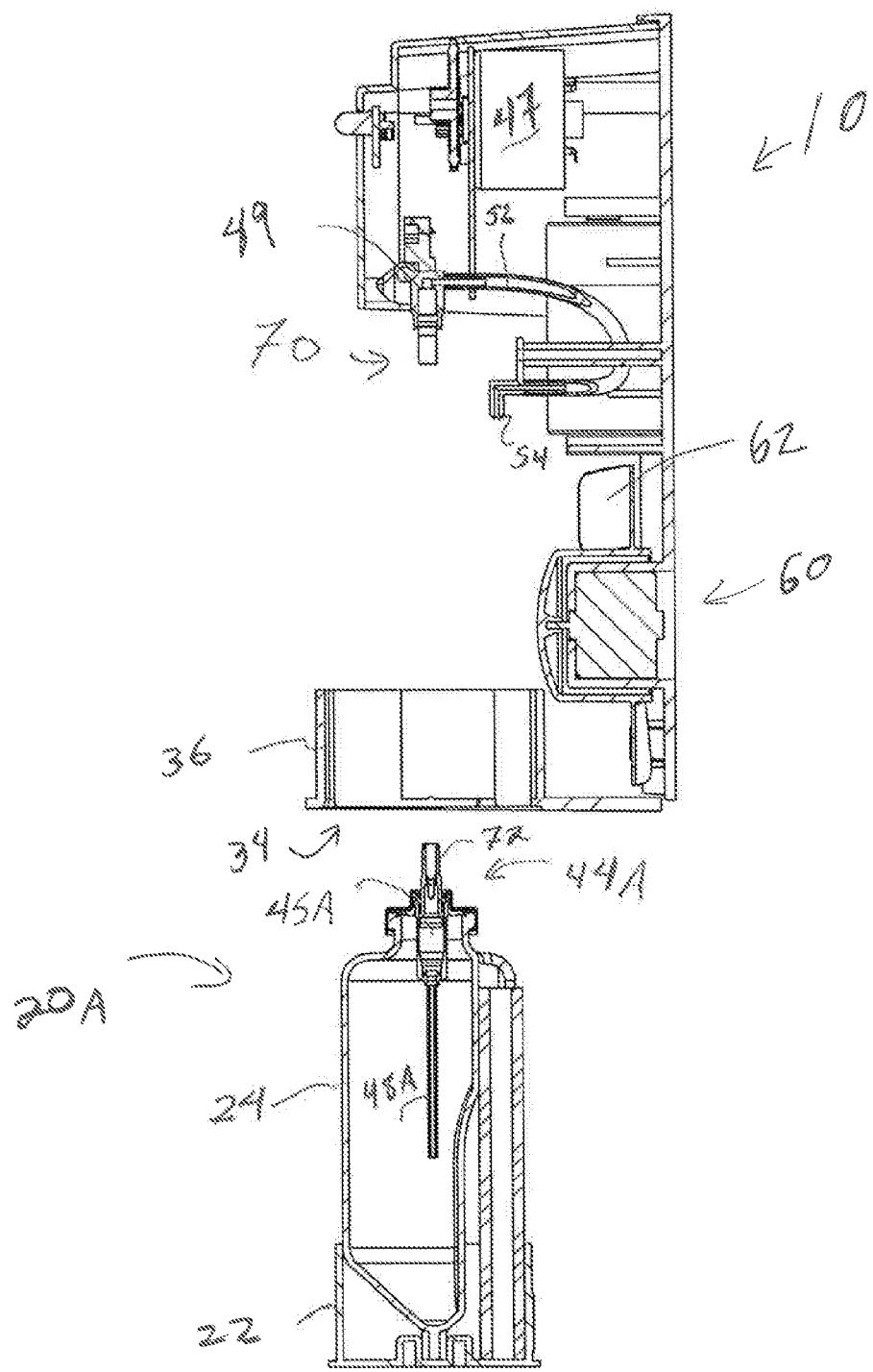

APPARATUS FOR METERED DOSE OF ODOR CONTROL SUBSTANCE

BACKGROUND

Numerous devices and approaches are known for dispensing fragrances for odor control purposes. The fragrances are dispensed from air control substances of varying types and forms, including gels, absorbent wicks, gases, liquids, and solids. It is known to incorporate these odor control substances in refill containers which are utilized with dispenser housings or supports. Some prior art dispensers are electrically powered, employing fans and/or heating elements to promote fragrance dispensing.

A need exists for an environmentally friendly metered control for dispensing odor control substances such as fragrances in an optimized manner with relatively limited waste.

SUMMARY

The present disclosure provides an apparatus. In an embodiment, an apparatus for dispensing the fragrance of an odor control substance is provided and includes A. a housing defining an interior, the housing interior adapted to receive a refill component. The refill component comprises
 (i) a support structure supporting
 (ii) a container containing a liquid odor control substance, and
 (iii) a wick extending along an exterior side of the container.

B. The housing interior contains a pump device. The pump device includes an inlet and an outlet. The pump inlet is in fluid communication with the liquid odor control substance. A controller is in operative communication with the pump device. A tube extends from the pump outlet and has a discharge end that is in cooperative relation with a wicking area of the refill component.

C. The controller operates the pump device to dispense a dose of the liquid odor control substance through the tube end and into the wicking area.

The present disclosure provides another apparatus. In an embodiment, an apparatus for dispensing the fragrance of an odor control substance is provided and includes A. a housing defining an interior, the housing interior adapted to receive a refill component. The refill component comprises
 (i) a support structure supporting
 (ii) a container containing a liquid odor control substance, and a pump device attached to an opening of the container; the pump device is in fluid communication with the liquid odor control substance, and
 (iii) a wick extending along an exterior side of the container.

B. The housing interior contains a port adapted to receive the pump device when the refill component is installed into the housing interior. A controller is in operative communication with the pump device, when the pump device is in fluid communication with the port. A tube extends from the pump outlet and having a discharge end in cooperative relation with a wicking area of the refill component.

C. The controller operates the pump device to dispense a dose of the liquid odor control substance through the tube end and into a wicking area.

BRIEF DESCRIPTION OF THE DRAWINGS

FIG. 6 is a side elevation view of a refill component in accordance with another embodiment of the present disclosure.

FIG. 7 is an exploded perspective view of the refill component of FIG. 6.

FIG. 8 is a sectional view of the housing and the alternate embodiment of the refill component of FIG. 6.

DETAILED DESCRIPTION

Figure 1:
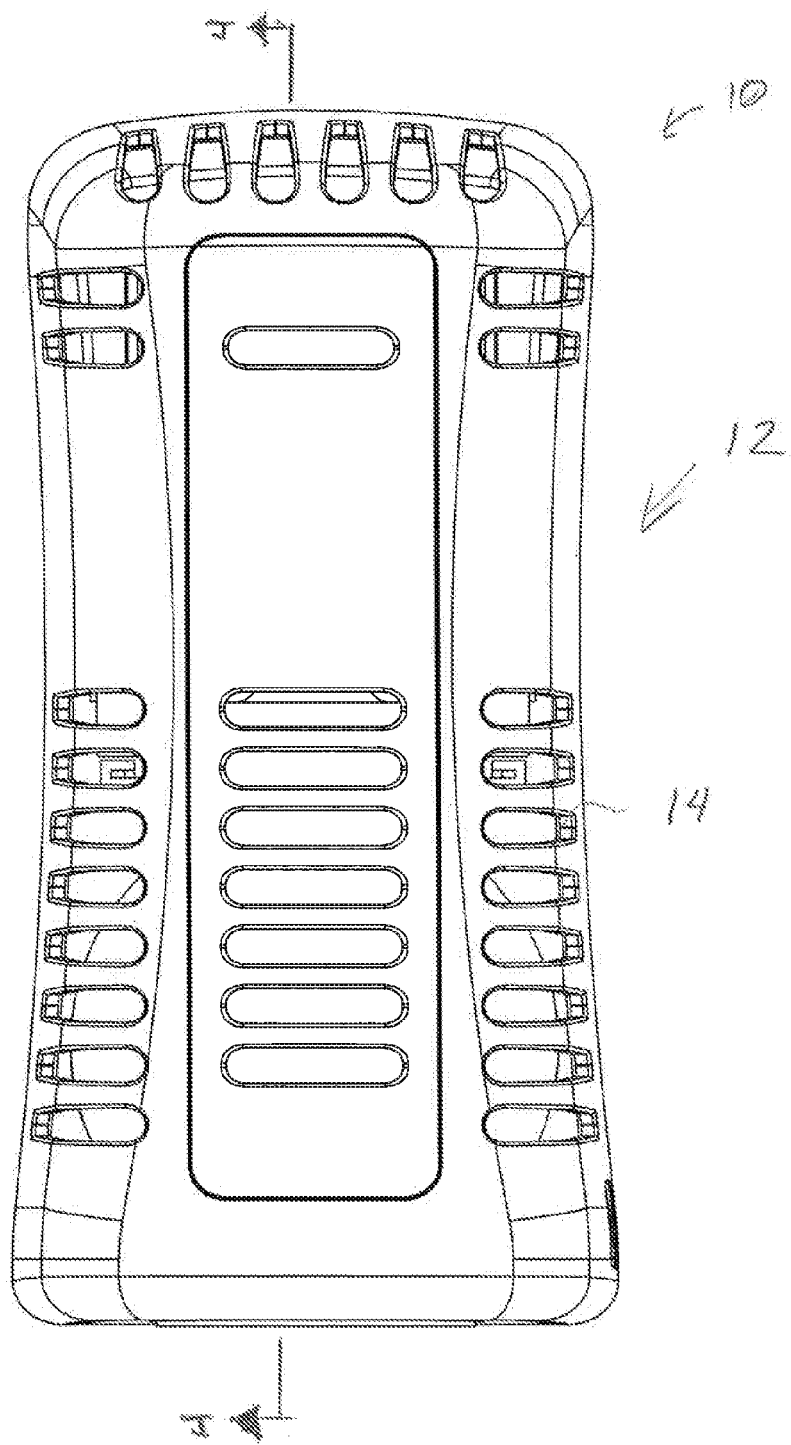
FIG. 1 is a front elevation view of an apparatus for dispensing the fragrance of an odor control substance in accordance with an embodiment of the present disclosure.

Referring now to FIGS. 1-8, an apparatus 10 for dispensing the fragrance of an odor control substance is provided. The apparatus 10 includes a housing 12 which defines a housing interior. The housing 12 includes a cover 14 and a panel 16. The cover has vents 18. The panel 16 has structure to secure and support components located in the housing interior. In addition, the panel 16 includes structure that enables the housing 12 to be mounted to a surface such as a wall, a ceiling, a door, or a floor.

1. Housing with Pump

Figure 2:
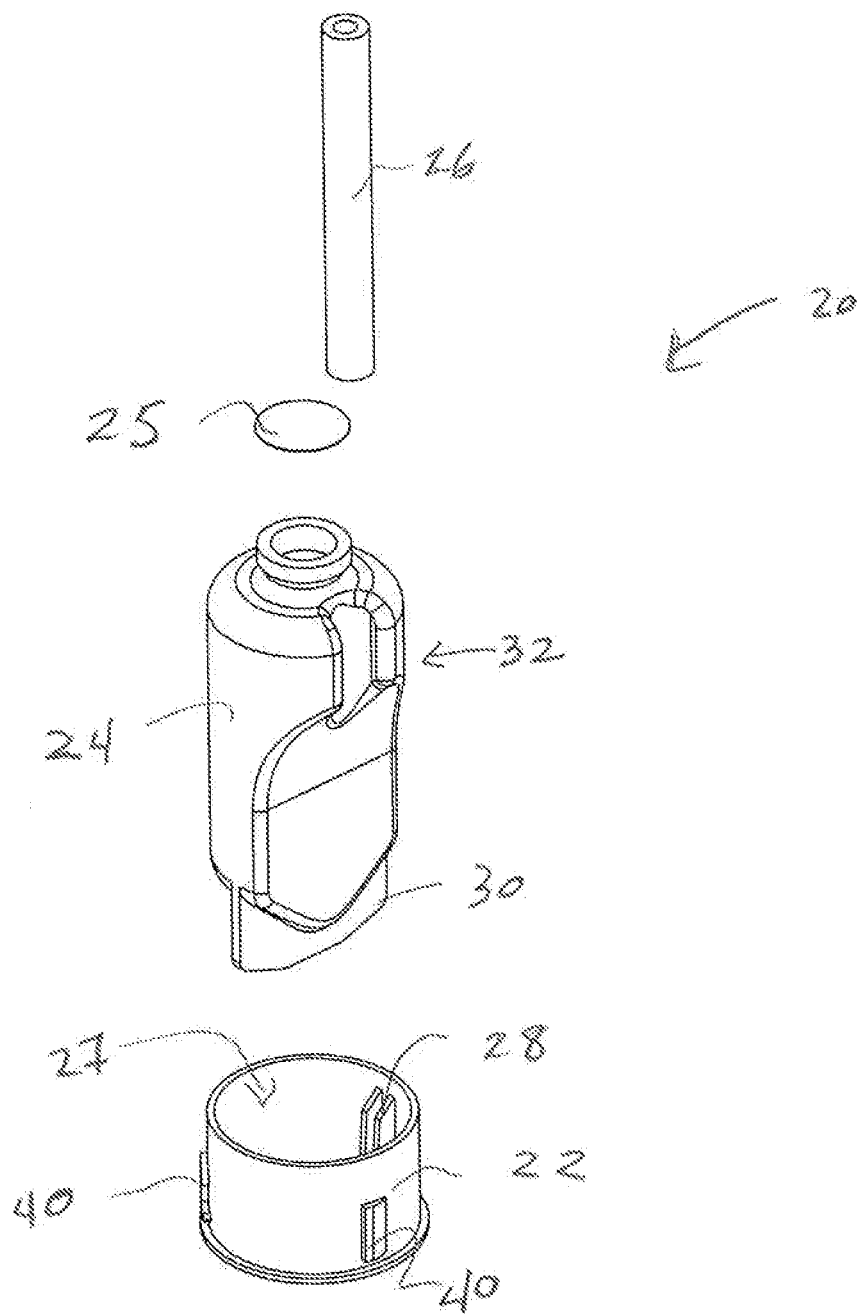
FIG. 2 is an exploded perspective view of a refill component in accordance with an embodiment of the present disclosure.

The housing interior is adapted to receive a refill component 20. As shown in FIG. 2, the refill component 20 includes a support structure 22. The support structure 22 supports a container 24, and a wick 26.

In an embodiment, the support structure 22 includes a slot 28 and the container includes a tab 30. The slot 28 and the tab 30 matingly engage in a friction-fit manner to hold or otherwise secure the container 24 firmly within the refill component 20.

The container 24 holds or otherwise contains a liquid odor control substance. In an embodiment, the liquid odor control substance includes a fragrance that is delivered from the apparatus 10.

In an embodiment, the container 24 holds from 60 milliliters (ml), or 70 ml, to 80 ml, or 90 ml, or 100 ml of the liquid odor control substance.

In an embodiment, the container 24 holds 73 ml of liquid odor control substance.

In an embodiment, the container 24 includes a seal 25. The seal 25 keeps the liquid odor control substance in the container during storage and transport. The seal 25 is removed (or is pierced) prior to or during installation of the refill component 20 into the housing 12 (as will be discussed below). In a further embodiment, the seal 25 is heat sealed to the opening of the container 24.

In an embodiment, the container 24 is configured to include a cusp 32 that engages the wick 26 in a friction-fit manner to hold the wick 26 firmly within the refill component 20.

The wick 26 extends along an exterior side of the container 24. The wick 26 is made of an absorbent material. Nonlimiting examples of suitable materials include polymeric materials, cellulosic-based materials (paper), fabrics (natural, synthetic), polyester, polyolefins, nylon, acetate, foams (hydrophilic polyurethane), polyolefins, polyamides, acrylics, styrenes, and any combination of the foregoing.

In an embodiment, the wick 26 includes a porous material, such as a porous plastic, a foam, or a porous fiber.

The wick may have a uniform structure. Alternatively, the wick may have a hollow interior, or a cored-out interior, such as a tubular shape.

In an embodiment, the wick 26 is cylindrical, or substantially cylindrical, in shape.

The wick 26 is external to the container 24. When the refill component 20 is not installed in the housing (storage, transport), the wick 26 is dry. The liquid odor control substance is later dosed onto the wick 26. Keeping the wick 26 dry and out of contact with the liquid odor control substance until installation advantageously improves shelf life of the refill component, eases fill and re-fill of the container 24, and optimizes performance of the apparatus 10.

Figure 3:
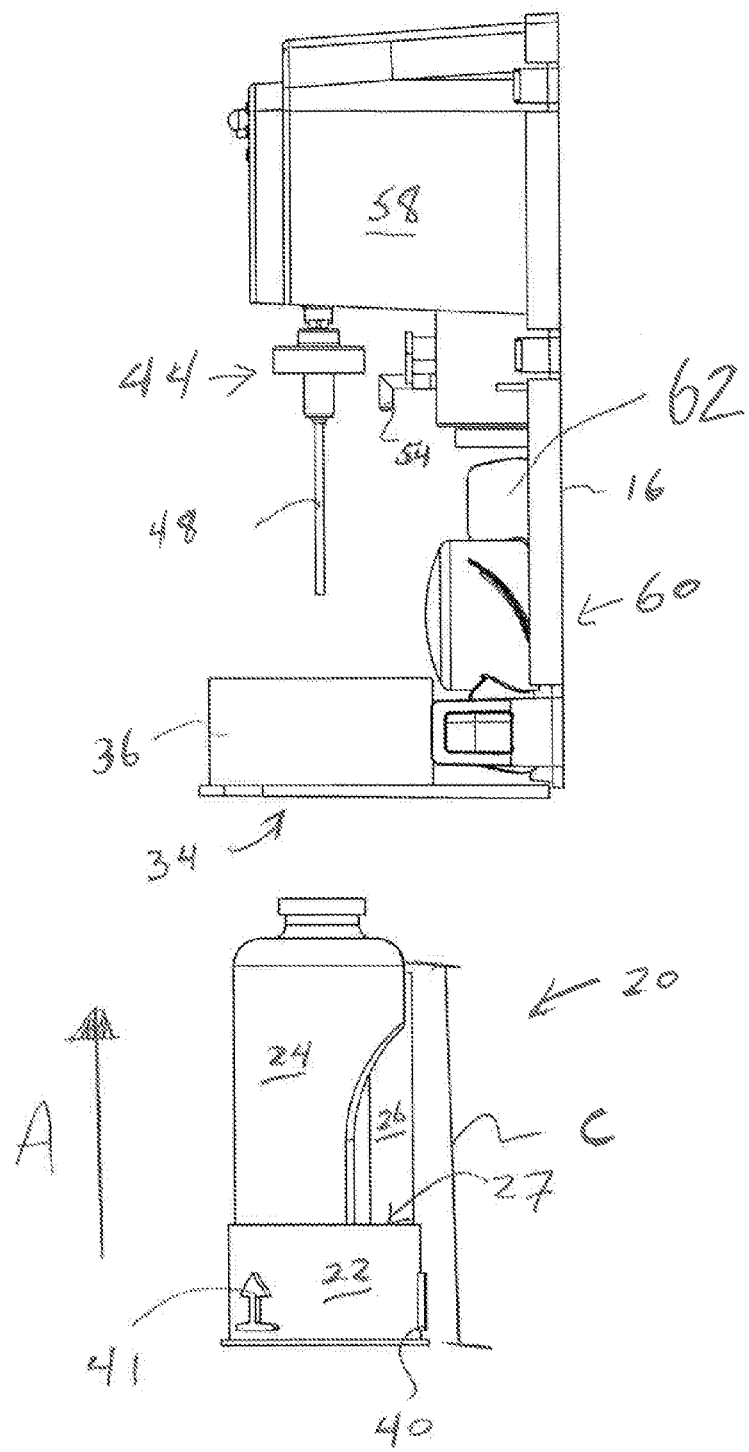
FIG. 3 is a partial break-away view of the housing and a side elevation view of the housing and the refill component before installation and in accordance with an embodiment of the present disclosure.
Figure 4:
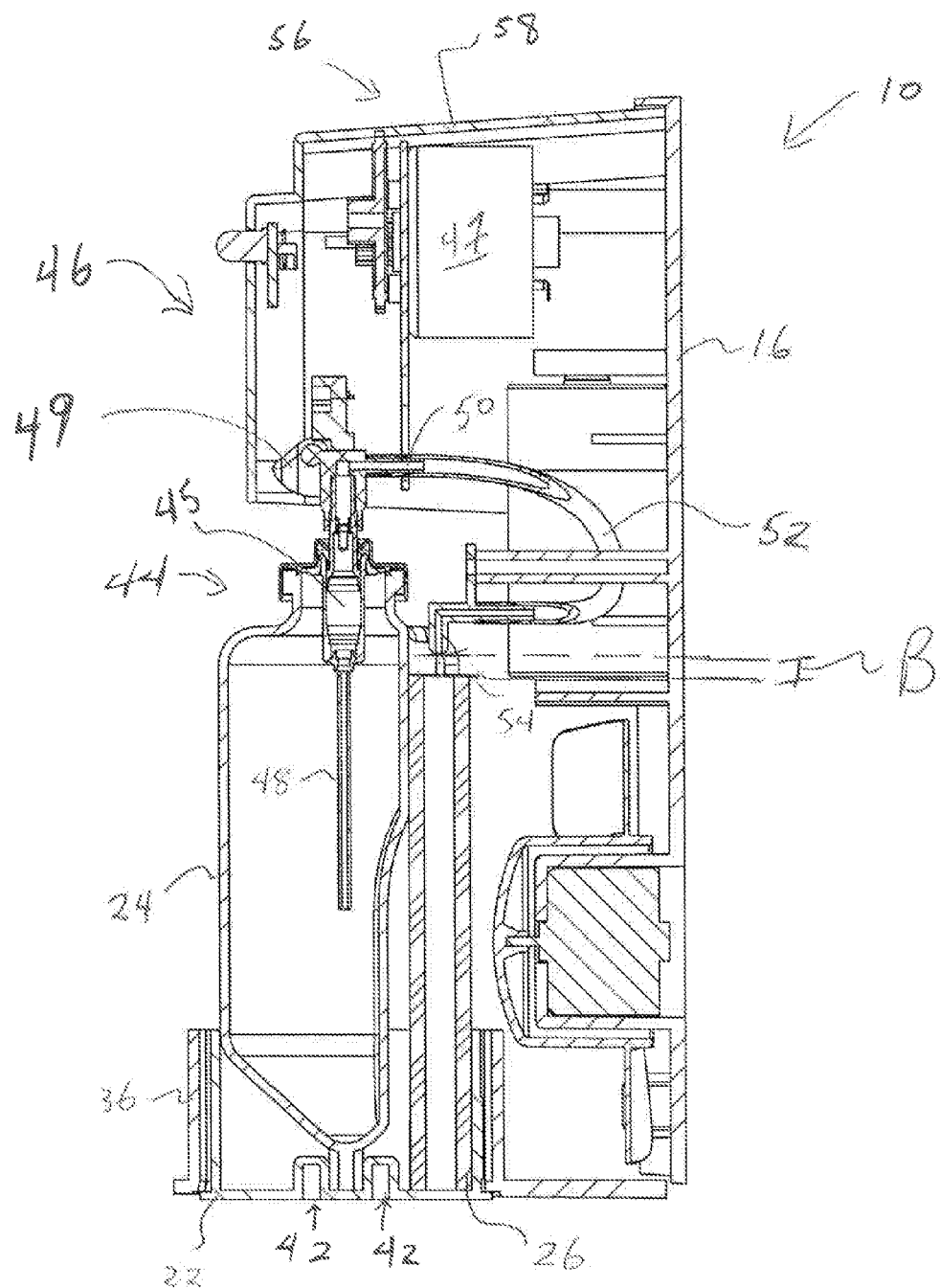
FIG. 4 is a sectional view taken along line 4-4 of FIG. 1.
Figure 5:
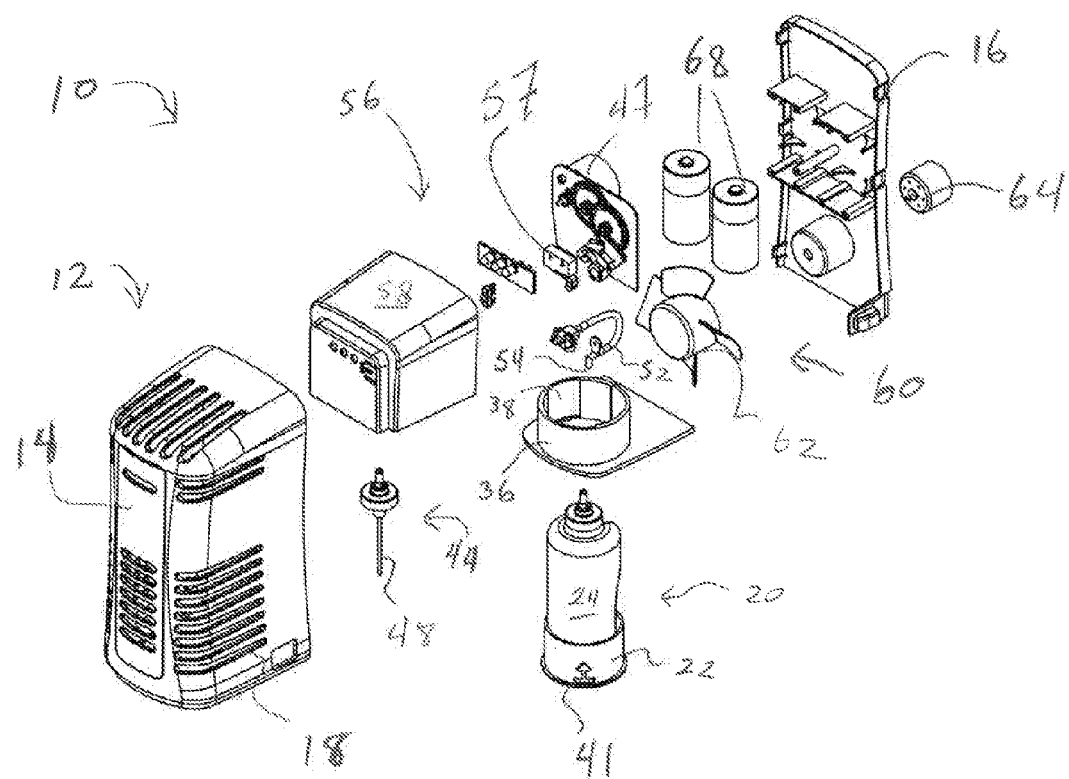
FIG. 5 is an exploded perspective view of the apparatus of FIG. 1.

The bottom of the housing 12 includes a bottom opening 34. Projecting upwardly from the bottom opening 34 is a cylindrically-shaped wall 36. Wall 36 defines a plurality of female recesses 38 extending vertically as shown in FIGS. 3-5. The support structure 22 of the refill component 20 has a plurality of vertically extending spaced male members 40. In an embodiment, a male support member is in the shape of an upward arrow 41 as seen in FIGS. 3, 5, and 6. The female recesses 38 (FIG. 3) of the cylindrically-shaped wall 36 must match up with the male elements 40; otherwise the refill component 20 will be precluded from entering the confines of the cylindrically-shaped wall 36. That is, the refill component and the housing must have a predetermined compatible character to enable the refill component to move to operating position within the housing. Such an arrangement can be utilized as a lock out feature to ensure that the housing is being refilled by an appropriate refill component. The housing bottom can provide the refill compliancy, lock out functionality, and act to prevent a user from touching the liquid odor control substance and/or the wick 26.

To install the refill component 20, it is manually moved upwardly through the bottom opening 34. This can only be done when the male members 40 are aligned with female recesses 38. Movement is along a substantially vertical axis from a position wherein the refill component 20 is located below the housing in the direction of up-arrow A (see FIG. 3) to a position wherein the refill component 20 is located in the housing interior (see FIG. 4). Once the bottoms of the male members 40 clear the bottom wall of the housing, the refill component 20 is turned in one direction. Manual turning is facilitated by use of manually engageable elements in the form of indents 42 (FIG. 4) located at the bottom of the refill component 20. To remove the refill component 20, it is rotated in the opposite direction.

In an embodiment, the indents 42 are configured such that installation and removal of the refill component 20 is accomplished by inserting a uniquely-designed key device that mates with the indents 42, thereby providing lock out functionality.

Within the housing interior is a pump device 44 as seen in FIGS. 4 and 5. The pump device includes a pump 45 and an inlet 48. A drive device 46 with a motor 47 and an actuator/hammer component 49 compresses the pump 45 to drive the liquid odor control substance from the container 24, through the pump inlet 48, and through the outlet 50. A flexible tube 52 extends from the outlet 50. The flexible tube 52 has a discharge end 54.

The distal end of the pump inlet 48 is placed in fluid communication with the liquid odor control substance in the container 24. It is understood that the pump inlet 48 may be configured to extend to the bottom, or substantially to the bottom, of the container 24. In an embodiment, the distal end of the pump inlet 48 pierces the seal 25 of the container as the refill component 20 is installed into the housing interior through the bottom opening (as discussed above).

Also within the housing interior is a controller 56. The controller 56 is in operative communication with the pump device 44 and the drive device 46. The term "operative communication" as used herein, is connectivity that enables communication between two components. Nonlimiting examples of suitable of operative communication between the controller 56 and the pump device 44/drive device 46 include electrical communication, mechanical communication, electromechanical communication, and combinations thereof.

In an embodiment, the controller 56 directs the drive device 46 to initiate a motor 47 to drive a gear train which actuates the actuator/hammer component 49 to compress the pump 45 and pull liquid through the pump inlet 48 and into the flexible tube 52 and through the tube discharge end 54 as shown in FIG. 4.

The controller 56 includes suitable hardware and software (logic) to provide additional functionality to the apparatus 10. Nonlimiting examples of suitable components for the controller includes switches, indicators, sensors, solenoids, programmable logic control, circuitry, and combinations thereof. The components of the controller are protected by a controller cover 58.

In an embodiment, the controller controls a day/night sensor and light emitting diode (LED).

In an embodiment, the controller senses when the refill component is empty and turns on an LED to indicate the same. When a new refill component is installed, the controller automatically resets a dose counter by way of a microswitch 57 (FIG. 5). When fully installed in the housing interior, the refill component 20 contacts a microswitch 57 which is detected by the controller. The controller 56, triggered by the microswitch 57, then re-sets the dose counter for the new refill component. By resetting the dose counter, the controller/microswitch ensures that the LED "empty light" will function properly when the refill component eventually empties. Microswitch detection of refill component installation advantageously adds convenience (i) by eliminating the need to perform a manual reset of the "empty light" switch and (ii) eliminating the risk of forgetting to manually perform of manual switch.

In an embodiment, the controller includes one or more sensors, logic, and corresponding indicia (such as a lights or light emitting diodes) in operative communication therewith to detect (and indicate) one, some or all of the following operating parameters:

power on, power off of the apparatus 10;
    empty or non-empty refill component 20; and
    switches to select a pre-determined metered dose.
    day/night sensor which optimizes fragrance dispersion when only room is in use.

When the refill component 20 is installed and secured in the housing interior, a wicking area C (FIG. 3) of the refill component 20 is placed into cooperative relation with respect to the tube discharge end 54. The wicking area C includes the wick 26 and a reservoir 27 formed by the wall of the support structure 22. The term "cooperative relation," as used herein, is opposing orientation between the tube discharge end 54 and the wicking area C such that the wicking area C is positioned to receive the liquid odor control substance discharged from the tube discharge end 54. The tube discharge end 54 may dispense the liquid odor control substance onto the wick 26, into the reservoir 27, and onto both the wick 26 and the reservoir 27.

In an embodiment, the cooperative relation includes the tube discharge end 54 directly opposing a topmost wick surface (i.e., no intervening components or structures therebetween), the distance between the tube discharge end 54 and the topmost wick surface being a distance B as shown in FIG. 4. In an embodiment, distance B is from 0.1 mm to 1.0 mm.

In an embodiment, the controller 56 directs the pump device 44 to dispense a dose of the liquid odor control substance through the tube discharge end 54 and onto the wick 26. A "dose" as used herein, is the amount of the liquid odor control substance retrieved from the container 24 through the pump inlet 48, by way of the pump device 44, through the tube discharge end 54 and onto the wick 26. A dose can be in the form of a drip, a spray, a mist, a stream, and any combination thereof. The liquid odor control substance is absorbed by the wick 26 and moves from the wick 26 to the ambient environment by way of evaporation (liquid to gas) and capillary effect. The support structure 22 forms the reservoir 27 to capture any excess liquid odor control substance not captured by the wick 26. The wick 26 can utilize capillary action to provide the fragrance/odor control substance to the environment.

In an embodiment, the tube discharge end 54 drips (continuously or intermittently) liquid odor control substance into the reservoir 27, whereby the wick 26 absorbs the liquid odor control substance from the reservoir 27. In this way, fragrance can be built up in the system and start to accumulate in the reservoir 27 faster than in the wick 26, providing a supply of fragrance to disperse.

In an embodiment, the controller and the pump device are configured such that the tube discharge end 54 delivers a metered dose of the liquid odor control substance to the wick 26. A "metered dose," as used herein, is (i) a pre-determined amount of the liquid odor control agent dispensed onto the wick 26, (ii) a pre-determined rate at which the liquid control agent is dispensed onto the wick 26, and (iii) a combination of (i) and (ii). The controller and the pump device can be programmed to obtain the parameters (i) and (ii) of a metered dose as desired.

In an embodiment, the apparatus 10 is configured to deliver a metered dose of fragrance at a regular interval from 10 days, or 20 days, or 30 days, or 40 days, or 50 days, or 60 days, or 70 days, to 80 days, or 90 days, or 100 days, or more.

In an embodiment, the controller coordinates and adjusts the metered dose in conjunction with the day/night sensor. During the day, the controller increases the metered dose and correspondingly decreases the metered dose when the day/night sensor detects night. This efficiently delivers more fragrance during higher traffic periods and decreases fragrance use during off-hours and therefore extends use of the refill component.

In an embodiment, the apparatus 10 is configured to deliver a metered dose of fragrance at a regular interval such that the amount of the liquid odor control agent in the container 24 will be evenly dispensed over a period from 10 days, 20 days, or 30 days, of 40 days, or 50 days, or 60 days, or 70 days, to 80 days, or 90 days, or 100 days, or more.

In an embodiment, the apparatus 10 includes a fan device 60 in the housing interior. The fan device 60 includes fan blades 62 and a fan motor 64. The vents 18 allow the passage of air simultaneously into and out of the housing interior due to operation of the fan device 60. Air drawn into the housing interior past the wick 26 entrains the fragrance of the liquid odor control substance and dispenses the fragrance from the housing and to an area (such as a room or a rest room, for example). The fan device 60 may or may not be placed into operative communication with the controller 56. An advantage of the present apparatus that due to capillary affect, even when fan device is not on to help disperse the fragrance, the wick 26 is still dispersing the fragrance. If a room (such as a washroom) has good air flow, patrons still experience the pleasure of smelling the fragrance from the apparatus 10, giving the impression that the apparatus 10 is "always on."

In an embodiment, the fan device is placed in operative communication with the controller 56. The controller 56 coordinates operation of the fan device with dosing to efficiently deliver fragrance to a room. Applicant discovered that synchronizing the metered dosing with fan operation can advantageously provide efficient odor control to a room by using less fragrance than required with a similar device dispensing fragrance with a fan alone.

In an embodiment, and as seen in FIG. 2, the surface of the container 24 that faces the fan blades 62 is flattened so as to maximize air flow and circulation around the wick 26. The surface configuration of the container 24 advantageously contributes to effective delivery of the fragrance to the ambient environment (such as a rest room, for example).

In an embodiment, the apparatus 10 includes a power source. The power source may be conventional A/C power from a utility power supply. In another embodiment, the power source for the apparatus 10 is one or more batteries 68 as shown in FIG. 5. The batteries may be placed in operative communication with the controller, the pump device, the fan device and any combination thereof.

In an embodiment, the power source is a solar cell.

2. Refill Component with Pump

In an embodiment, as shown in FIGS. 6-8, a refill component 20A includes the support structure 22, the container 24, and the wick 26, as discussed above. The refill component 20A also includes a pump device 44A attached to the opening of the container 24. The pump device 44A includes a pump 45A and an inlet 48A. The pump device 44A is replaceable or is otherwise reusable. In this embodiment, the pump device is 44A is packaged with the refill component 20A. During storage and transport of the refill component 20A, a cap 66 covers the pump device 44A for protection.

When the refill component 20A is installed into the apparatus 10, the cap 66 is removed. In the housing interior, a port 70 is adapted to receive a head 72 of the pump 44A. The port is in operative communication with the drive device 46. The port 70 and the head 72 are configured for intimate (watertight) fluid communication when the refill container 20A is installed in the housing interior. Once the refill component 20A is installed within the housing interior, the pump device 44A operates in the same manner as discussed above.

Replacing the refill component 20A simultaneously replaces the pump device 44A advantageously extending the longevity and operational life of the apparatus 10.

The present apparatus may comprise two or more embodiments disclosed herein.

DEFINITIONS

The terms "comprising", "including", "having" and their derivatives do not exclude the presence of any additional component, or procedure. The term, "consisting essentially of" excludes any other component or procedure, except those essential to operability. The term "consisting of" excludes any component, procedure not specifically stated.

It is specifically intended that the present disclosure not be limited to the embodiments and illustrations contained herein, but include modified forms of those embodiments including portions of the embodiments and combinations of elements of different embodiments as come within the scope of the following claims.

What is claimed is:

1. An apparatus for dispensing the fragrance of an odor control substance comprising:
 A. a housing defining an interior, the housing interior adapted to receive a refill component, the refill component comprising
  (i) a support structure supporting
  (ii) a container containing a liquid odor control substance, and
  (iii) a wick extending along an exterior side of the container;
 B. the housing interior containing
  a pump device comprising an inlet and an outlet, the pump inlet in fluid communication with the liquid odor control substance;
  a controller in operative communication with the pump device;
  a tube extending from the pump outlet and having a discharge end in cooperative relation with a wicking area of the refill component; and
 C. the controller operates the pump device to dispense a dose of the liquid odor control substance through the tube end and into the wicking area.

2. The apparatus of claim 1 wherein the pump device dispenses a metered dose of the liquid odor control substance onto the wick.

3. The apparatus of claim 1 wherein the housing comprises a plurality vents for allowing the passage of air in and out of the housing interior.

4. The apparatus of claim 1 comprising a fan device in the housing interior, the fan device drawing air into the housing interior and past the wick to dispense the odor control substance from the housing.

5. An apparatus for dispensing the fragrance of an odor control substance comprising:
 A. a housing defining an interior, the housing interior adapted to receive a refill component, the refill component comprising
  (i) a support structure supporting
  (ii) a container containing a liquid odor control substance, and a pump device attached to an opening of the container, the pump device in fluid communication with the liquid odor control substance, and
  (iii) a wick extending along an exterior side of the container;
 B. the housing interior containing
  a port adapted to receive the pump device when the refill component is installed into the housing interior;
  a controller in operative communication with the pump device in the port;
  a tube extending from the pump outlet and having a discharge end in cooperative relation with a wicking area of the refill component; and
 C. the controller operates the pump device to dispense a dose of the liquid odor control substance through the tube end and into the wicking area.

* * * * *

UNITED STATES PATENT AND TRADEMARK OFFICE
CERTIFICATE OF CORRECTION

| | | |
|---|---|---|
| PATENT NO. | : 8,889,082 B2 | Page 1 of 1 |
| APPLICATION NO. | : 13/843991 | |
| DATED | : November 18, 2014 | |
| INVENTOR(S) | : Todd J. Muderlak, Kenneth J. Muderlak and Roland E. C. Schwarz | |

It is certified that error appears in the above-identified patent and that said Letters Patent is hereby corrected as shown below:

ON THE TITLE PAGE

Item (72) Inventor: Please add – Roland E.C. Schwarz.

Signed and Sealed this
Ninth Day of February, 2016

Michelle K. Lee
*Director of the United States Patent and Trademark Office*